(12) United States Patent
McLaughlin et al.

(10) Patent No.: US 11,246,487 B2
(45) Date of Patent: Feb. 15, 2022

(54) METHOD FOR CHARACTERISING A MECHANICAL PROPERTY OF A MATERIAL

(71) Applicant: THE UNIVERSITY OF WESTERN AUSTRALIA, Crawley (AU)

(72) Inventors: Robert Ainsley McLaughlin, Bayswater (AU); Kelsey Marie Kennedy, Como (AU); Brendan Francis Kennedy, Joondanna (AU); David Douglas Sampson, Claremont (AU)

(73) Assignee: The University of Western Australia, Crawley (AU)

( * ) Notice: Subject to any disclaimer, the term of this patent is extended or adjusted under 35 U.S.C. 154(b) by 1433 days.

(21) Appl. No.: 14/275,069

(22) Filed: May 12, 2014

(65) Prior Publication Data

US 2014/0316237 A1    Oct. 23, 2014

Related U.S. Application Data

(63) Continuation of application No. PCT/AU2012/001385, filed on Nov. 9, 2012.

(30) Foreign Application Priority Data

Nov. 10, 2011  (AU) ............................... 2011904682

(51) Int. Cl.
*A61B 5/00* (2006.01)
*A61B 10/00* (2006.01)
(Continued)

(52) U.S. Cl.
CPC .......... *A61B 5/0053* (2013.01); *A61B 5/0048* (2013.01); *A61B 5/0057* (2013.01);
(Continued)

(58) Field of Classification Search
None
See application file for complete search history.

(56) References Cited

U.S. PATENT DOCUMENTS 5,919,172 A * 7/1999 Golba, Jr. .......... A61B 17/3401
                                              604/164.01
8,342,851 B1 * 1/2013 Speeg .................. G09B 23/285
                                              434/267
(Continued)

FOREIGN PATENT DOCUMENTS

| WO | 2007/090147 | 8/2007 |
| WO | 2007/127228 | 11/2007 |
| WO | 2008/068685 | 6/2008 |

OTHER PUBLICATIONS

Friction by Wikipedia; pub. online on Nov. 2, 2011 at https://en.wikipedia.org/w/index.php?title=Friction&oldid=458563196.*

(Continued)

*Primary Examiner* — Katherine L Fernandez
*Assistant Examiner* — Michael S Kellogg
(74) *Attorney, Agent, or Firm* — Michael Best & Friedrich LLP

(57) ABSTRACT

A method for characterising a mechanical property of a material. The method comprises the steps of providing the material having a deformable portion and providing a device having an optical element that is arranged to detect electromagnetic radiation.

17 Claims, 9 Drawing Sheets

(51) Int. Cl.
  *A61B 90/30* (2016.01)
  *A61B 8/08* (2006.01)
(52) U.S. Cl.
  CPC .......... *A61B 5/0059* (2013.01); *A61B 5/0084* (2013.01); *A61B 5/0086* (2013.01); *A61B 5/442* (2013.01); *A61B 5/6848* (2013.01); *A61B 5/0051* (2013.01); *A61B 5/0066* (2013.01); *A61B 5/0091* (2013.01); *A61B 8/485* (2013.01); *A61B 10/0041* (2013.01); *A61B 2090/306* (2016.02)

(56) References Cited

U.S. PATENT DOCUMENTS

| | | | | |
|---|---|---|---|---|
| 2003/0045798 | A1* | 3/2003 | Hular | A61B 5/0066 600/476 |
| 2006/0058592 | A1* | 3/2006 | Bouma | A61B 5/0059 600/301 |
| 2009/0073453 | A1 | 3/2009 | Hasegawa | |
| 2009/0116032 | A1 | 5/2009 | Zara | |
| 2011/0066073 | A1 | 3/2011 | Kuiper et al. | |
| 2011/0112549 | A1 | 5/2011 | Neubach et al. | |

OTHER PUBLICATIONS

Dry lubricant by Wikipedia; pub. online on Oct. 15, 2011 at https://en.wikipedia.org/w/index.php?title=Dry_lubricant&oldid=455756968.*

Tribology by Wikipedia; pub. online on Oct. 27, 2011 at https://en.wikipedia.org/w/index.php?title=Tribology&oldid=457634070.*

Cuiru Sun et al., "Optical coherence elastography: current status and future applications",Journal of Biomedical Optics, Apr. 1, 2011 (14 pgs).

Supplementary Search Report for European Application 12848030.8 dated Aug. 19, 2015 (6 pgs).

Schmitt, J., "OCT elastograhy: imaging microscopic deformation and strain of tissue" Hong Kong University of Science and Technology Department of Electrical and Electronic Engineering, Optics Express, vol. 3, No. 6, Sep. 14, 1998 (13 pages).

Kirkland, S. et al., "OCT-based elastography for large and small deformations" Optics Express, vol. 14, No. 24, Nov. 27, 2006 (13 pages).

International Search Report for PCT/AU2012/001385 dated Jan. 4, 2013 (4 pages).

* cited by examiner

METHOD FOR CHARACTERISING A MECHANICAL PROPERTY OF A MATERIAL

BACKGROUND OF THE INVENTION

The present invention broadly relates to a method for characterising a mechanical property of a material, and relates particularly, not exclusively though, to a method for characterising an elasticity of biological tissue to characterise and/or locate cancerous tissue.

The treatment of cancer often requires surgical removal of cancerous tissue and it is important that the cancerous tissue is completely removed. Therefore it is important to have relatively precise information about location and size of a tumour for a successful treatment of cancer.

Cancerous tissue is usually "stiffer" than surrounding soft tissue and it is common practice that medical practitioners manually palpate the soft tissue of a patient by applying pressure with their fingers to identify such tumours.

It is common practice for a surgeon to use such manual palpation of tissue to delineate the extent of a tumour during surgical tumour resection. For example, remaining cancerous tissue of a patient who undergoes treatment of cancer can be identified. An additional margin of healthy tissue around a tumour is typically removed to minimise residual malignancy and therefore minimise local recurrence of the cancer. However, accurate identification of the extent of the tumour is difficult during surgery. In the example of breast cancer, it has been reported that up to 34% of patients undergoing breast-conserving surgery will have involved margins or inadequate clearance. These patients may face an increased risk of recurrence of the tumour that often results in additional surgery or aggressive chemotherapy.

SUMMARY OF THE INVENTION

The present invention provides in a first aspect a method for characterising a mechanical property of a material, the method comprising the steps of:

providing the material having a deformable portion;

providing a device having an optical element that is arranged to detect electromagnetic radiation, the device further comprising an insertion portion that is arranged for insertion into the deformable portion of the material and the device being arranged such that the electromagnetic radiation is detectable by the optical element at a location within the deformable portion;

moving the insertion portion of the device within the deformable portion of the material in a manner such that the deformable portion is deformed;

emitting electromagnetic radiation into the material such that propagation of the electromagnetic radiation through the material is influenced by the mechanical property of the material associated with a deformation of the deformable portion;

detecting the electromagnetic radiation in response to the emitted electromagnetic radiation using the optical element at the location within the deformable portion; and analysing the detected electromagnetic radiation to characterise the mechanical property of the material.

The term "material" as used herein is intended to encompass any matter that has a mechanical property such as an elasticity, a viscosity or a viscoelasticity, including, for example, non-biological material such as silicone and biological material such as biological tissue.

The step of emitting the electromagnetic radiation into the material may be conducted when the deformable material is being deformed. Alternatively, the step of emitting the electromagnetic radiation into the material may be conducted before and/or after the deformable portion has been deformed.

In one particular embodiment, the method comprises further the steps of:

detecting electromagnetic radiation in response to the emitted electromagnetic radiation during and after deforming using the optical element at the location within the deformable portion of the material; and comparing a quantity indicative of the electromagnetic radiation detected during the deformation with a quantity indicative of the electromagnetic radiation detected after the deformation;

wherein a result of comparing the quantities is indicative of the mechanical property of the material.

Based on the characterised mechanical property of the material, a location of an interface between two different types of material portions may be identified.

In one embodiment the optical element is also arranged to emit electromagnetic radiation and the step of emitting the electromagnetic radiation comprises emitting the electromagnetic radiation into the material using the optical element.

In a specific embodiment, the mechanical property is an elasticity, a viscosity or a viscoelasticity.

In a specific embodiment, the material is biological tissue, such as soft tissue of a human or an animal. The soft tissue may be accompanied by, or may comprise diseased tissue such as cancerous tissue. Specific examples for soft tissue may be fat and muscle.

For ease of understanding, the term "diseased" is used throughout the patent specification as a synonym for an abnormality in the tissue including a lesion or a tumour that may be benign, pre-malignant or malignant.

Alternatively, the material may be non-biological material such as silicone or any other suitable material.

In regard to biological tissue, it is known that cancerous tissue usually has a lower elasticity than healthy tissue. As mentioned above, medical practitioners use this knowledge to locate cancerous tissue by applying pressure on a tissue and manually palpating the tissue for abnormal stiff lumps. Abnormal stiff lumps may subsequently be identified as cancerous tissue.

The device typically is a medical device and may comprise a medical needle or an endoscope. In one specific embodiment the insertion portion of the device comprises a needle portion such as a tip of a needle. The needle portion may be part of a medical needle such as a hypodermic needle. The optical element may be arranged in or in proximity to the tip of the needle and may consequently be relatively narrow, which facilitates insertion of the insertion portion into the biological tissue to a location within the tissue that may not be accessible with manual palpation.

Embodiments of the present invention have significant advantages. Based on the characterised mechanical property of the biological tissue, the biological tissue may be characterised as, for example, healthy tissue or diseased tissue. The diseased tissue may be in the form of a benign or malignant tumour and may relate to any type of cancer such as breast cancer, head and neck cancer, and prostate cancer. Such a characterisation may be used to identify a location and/or an extent of cancerous tissue such as a breast tumour and/or a degree of severity of a disease. In this particular application, the mechanical property of the biological tissue may be characterised in vivo. In particular, a boundary of a tumour may be identified which may be used as guidance for excising the tumour. Furthermore, by characterising the mechanical property of the biological tissue, a location of an interface between two different types of tissue portions may be identified. Further, the tissue portion of interest of the biological tissue may be characterised before the tissue is excised during surgery.

The method in accordance with an embodiment of the present invention may be conducted in substantially real time.

As mentioned above, one exemplary advantageous application of the method is the characterisation of biological tissue of a patient to locate cancerous tissue. However, a person skilled in the art will appreciate that the method may be used for any other suitable application in the field of medicine or other fields of technology.

The device may comprise an optical fibre positioned at least partially within the needle portion and arranged for transmitting electromagnetic radiation from the optical element. Additionally, the optical fibre may be arranged for transmission of electromagnetic radiation to the optical element. The optical fibre may connect the optical element to an optical processing system and/or to a light source.

The deformable portion of the material may be deformed as a result of force applied by the insertion portion on the deformable portion of the material. The force applied by the insertion portion typically includes a component that results from friction between the insertion portion and the deformable portion of the material.

In one particular embodiment, the step of inserting the insertion portion into the deformable portion of the material is conducted in a manner such that the deformable portion is deformed by movement of the needle portion. For example, the movement may include advancing and/or retracting and/or rotating the insertion portion in one or more direction(s) within the deformable portion of the material. The movement may be a periodic movement such as a vibration.

In a specific embodiment, a surface of the insertion portion comprises a coating that is arranged to influence friction between the insertion portion and the deformable portion of the material. The coating may increase or decrease the friction between the insertion portion and the deformable portion compared with the friction between the insertion portion and the deformable portion without the coating.

In one particular embodiment, the device may comprise an endoscope and the step of inserting the insertion portion into the deformable portion of the material may be conducted in a manner such that the deformable portion is deformed by movement of the endoscope portion.

Some or all steps of the method may also be performed repeatedly, for example, to assess a change in the tissue in response to a medical treatment, such as radiation therapy or chemotherapy.

The method may be conducted using any suitable imaging technique to characterise a mechanical property of the material. For example, the method may be conducted using optical coherence tomography or confocal fluorescence microscopy.

In one particular example the emitted electromagnetic radiation may be infrared light such as near-infrared light.

The optical element may be arranged to emit the electromagnetic radiation in any suitable direction. In one specific embodiment the optical element is arranged to emit the electromagnetic radiation in a direction that is either substantially parallel or substantially perpendicular to a central axis of the insertion portion.

In accordance with embodiments of the present invention, the method comprises a further step of processing the detected electromagnetic radiation. For example, the detected electromagnetic radiation may be converted into digital data that can be analysed further. The method may further comprise a step of comparing the detected electromagnetic radiation to a database to characterise the mechanical property of the material.

In a further embodiment, the method comprises the step of providing an acoustic or visual indication of a presence of diseased tissue such as cancerous tissue in the proximity of the location within the deformable portion and based on the characterisation of the mechanical property.

In one embodiment, the method is conducted during surgery of a patient. The method may be conducted such that a location and/or an extent of diseased tissue, such as a tumour that may be cancerous, can be identified.

The present invention provides in a third aspect a medical device for characterising a mechanical property of biological tissue, a portion of the biological tissue being deformable, the medical device comprising:

an insertion portion for insertion into the deformable portion of the biological tissue in a manner such that the deformable portion of the biological tissue is deformed;

an optical element positioned on or in the insertion portion and arranged to receive electromagnetic radiation in response to electromagnetic radiation emitted into the biological tissue; and an optical fibre positioned at least partially within the insertion portion and arranged for transmission of electromagnetic radiation from the optical element.

The insertion portion may be a needle portion. Alternatively, the insertion portion may be an endoscopic portion or an intravascular portion.

The optical fibre may further be arranged for transmission of the electromagnetic radiation to the optical element.

In one specific embodiment, a surface portion of the insertion portion comprises a coating that is arranged to influence friction between the insertion portion and the deformable portion of the biological tissue. For example, friction may be increased or decreased compared with friction between the deformable portion of the biological tissue and the insertion portion without the coating.

The coating may comprise a plurality of coating portions and may be arranged such that friction between the insertion portion and the biological tissue is dependent on a location on the surface of the insertion portion.

The medical device may be one of a plurality of medical devices.

In a fourth aspect of the present invention, there is provided a method for characterising a mechanical property of a material, the method comprising the steps of:

providing the material having a deformable portion;

providing a device having an optical element that is arranged to detect electromagnetic radiation, the device further comprising an insertion portion that is arranged for insertion into the deformable portion of the material and the device being arranged such that the electromagnetic radiation is detectable by the optical element at a location within the deformable portion;

deforming the deformable portion of the material;

emitting electromagnetic radiation into the material such that propagation of the electromagnetic radiation through the material is influenced by the mechanical property of the material associated with a deformation of the deformable portion;

detecting the electromagnetic radiation in response to the emitted electromagnetic radiation using the optical element at the location within the deformable portion; and analysing the detected electromagnetic radiation to characterise the mechanical property of the material.

The material may be deformed in response to a force that is applied directly or indirectly to the deformable material portion. For example, if the material is biological tissue, the force may be a result of cardiac or respiratory motion.

The invention will be more fully understood from the following description of specific embodiments of the invention. The description is provided with reference to the accompanying drawings.

DETAILED DESCRIPTION

Embodiments of the present invention relate to a method for characterising a mechanical property of a material. Based on the characterised mechanical property, the a portion of the material may subsequently be characterised. For example, a location of an interface between two different material portions may be identified based on the characterised mechanical property. The material may be biological tissue and the method may be conducted such that a portion of the biological tissue is characterised as healthy or diseased tissue, which is usually stiffer than healthy tissue. Thus, boundaries of a structure, such as a tumour, may be identified. The method may be conducted during surgical treatment of cancer to identify a boundary of a tumour. However, a person skilled in the art will appreciate that the present invention has many different applications.

For example, the method may also be used to characterise or identify atherosclerotic plaques; diseased lung tissue; muscular dystrophy; damaged tissue in the heart due to ischemia; or for an assessment of oedema such as lymph oedema. A person skilled in the art will appreciate that the material may alternatively be non-biological material and the method has applications in various other fields.

Figure 1:
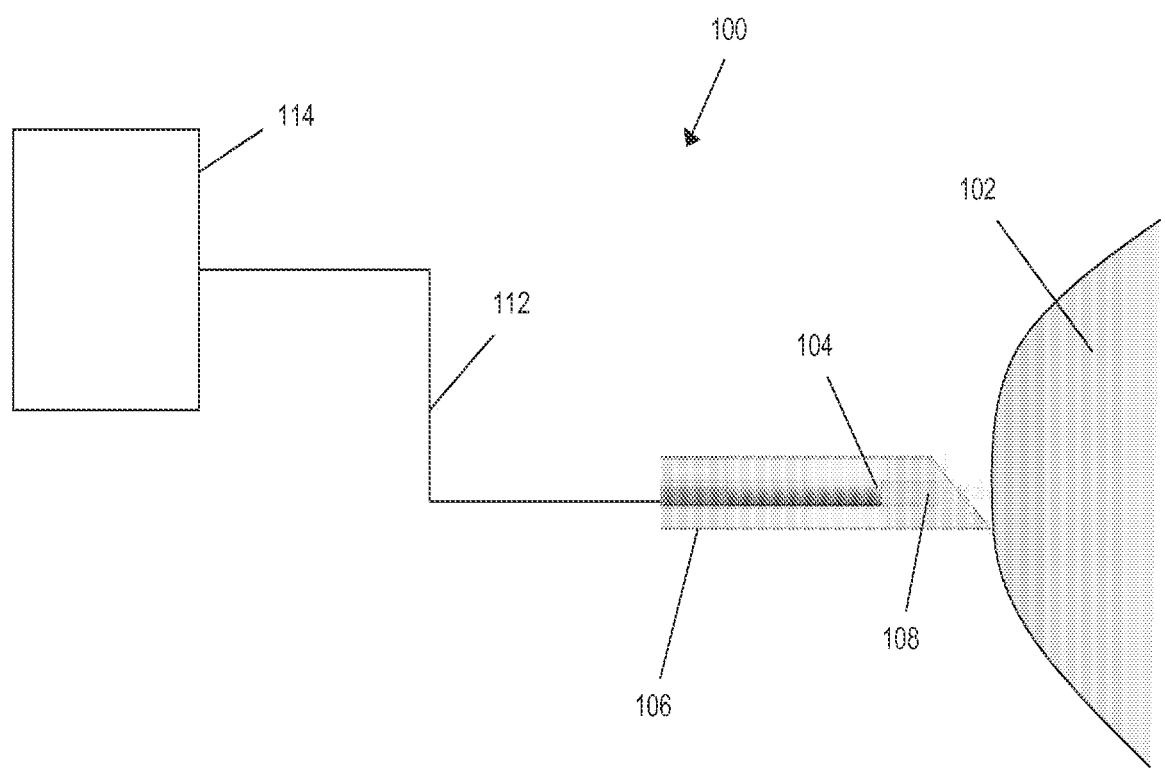
FIG. 1 is a schematic representation of a system for performing a method for characterising a mechanical property of a material in accordance with an embodiment of the present invention.

Referring now to FIG. 1, there is shown a system 100 arranged for characterising a mechanical property of biological tissue 102, such as breast tissue.

Biological tissue comprises a plurality of portions of tissue and each portion may have a different mechanical property.

As mentioned above, one particular application of an embodiment of the present invention relates to locating diseased tissue such as cancerous tissue. It is known that, for example, cancerous breast tissue is typically stiffer than surrounding healthy tissue. Furthermore, it is common practice for medical practitioners to apply manual pressure to breast tissue to identify stiff lesions that may subsequently be identified as cancerous tissue. For example, it has been reported that the Young's modulus of breast tumours may vary by up to a factor of 90 in comparison to healthy tissue.

Mechanical properties of a material define how the material behaves in response to an applied force. By characterising a mechanical property of a material at a location such as by calculating a local displacement, it is possible to derive information about a structure, a portion or a classification of the material at the location. Such a mechanical property may, for example, be an elasticity of a material, a viscosity or a viscoelasticity.

The method in accordance with embodiments of the present invention combines elastography with an imaging technique and an optical element for the imaging technique provided in or on an insertion portion of a device such as a tip of a medical needle arranged for insertion into a deformable portion of tissue material. The insertion portion is inserted into the deformable portion of the material in a manner such that the deformable portion of the material is deformed. In other words, the force for deforming the material is applied by virtue of the insertion portion of the device.

Figure 2:
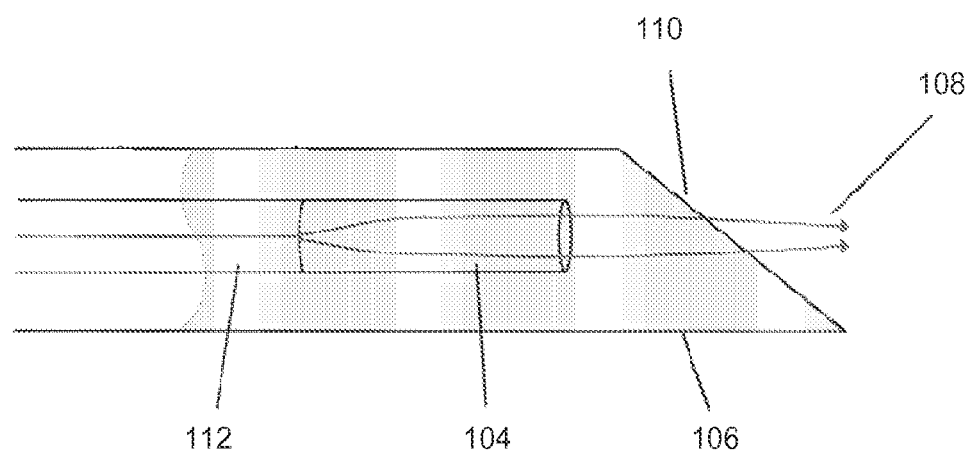
FIG. 2 is a schematic cross-sectional view of a tip of a needle comprising an optical element in accordance with an embodiment of the present invention.

Referring back to FIG. 1, an optical element 104 is positioned in a tip of a medical needle 106. The tip of the needle 106 can be inserted into a deformable portion of the tissue 102. A more detailed view of the tip of the needle 106 is shown in FIG. 2. The needle 106 in this particular embodiment is a hypodermic needle that comprises the optical element 104 in the tip of the needle 106.

In this embodiment, the optical element 104 is arranged to emit electromagnetic radiation 108 into the tissue 102 at a location within the deformable portion when the needle tip 106 is inserted into the deformable portion of the tissue 102. In this particular embodiment, the electromagnetic radiation 108 is near-infrared light. However, a person skilled in the art will appreciate that the electromagnetic radiation can be any suitable light such as infrared light, visible light or ultraviolet light. Furthermore, a person skilled in the art will appreciate that the electromagnetic radiation 108 may alternatively be emitted by any suitable source outside the needle tip 106.

The near-infrared light 108 is emitted in a direction that is parallel to a central axis of the tip of the needle 106, for example, through an optical window 110. A person skilled in the art will appreciate that alternatively the optical element 104 may emit the light 108 in any suitable direction into the deformable portion of the tissue 102. For example, the tip of the needle 106 may comprise an optical window 110 at a side of the needle such that the light 108 is emitted in a direction perpendicular to the central axis of the needle tip 106.

The optical element 104 may also be movable in or on the tip of the needle 106 such that a position of the optical element 104 within the needle or a direction of the emitted light 108 can be changed. For example, the tip of the needle 106 may comprise an optical window 110 at a side of the needle that is larger than the width of the light beam 108. By moving (translating and/or rotating) the optical element 104, the emitted light 108 may be emitted through different portions of the optical window 110. Thus, measurements of a plurality of portions of the deformable portion of the tissue 102 may be facilitated without moving the needle 106.

Near-infrared light 108 emitted from the optical element 104 propagates into the deformable portion of the tissue 102 and a portion of the light 108 is back-scattered by the tissue 102. For near-infrared light, the maximum distance into biological tissue, from which backscattered light can be detected to form an image, is approximately 2-3 mm. This maximum distance for the detection of the backscattered light determines the imaging field-of-view.

In this embodiment, the optical element 104 is arranged to detect electromagnetic radiation that is back-scattered by the tissue 102 in response to the emitted near-infrared light 108 at the location within the deformable portion of the tissue 102.

In this particular example, the method is conducted such that a signal is detected at the optical element 104 which is indicative of the optical backscattering as a function of distance from the optical element 104.

Figure 3:
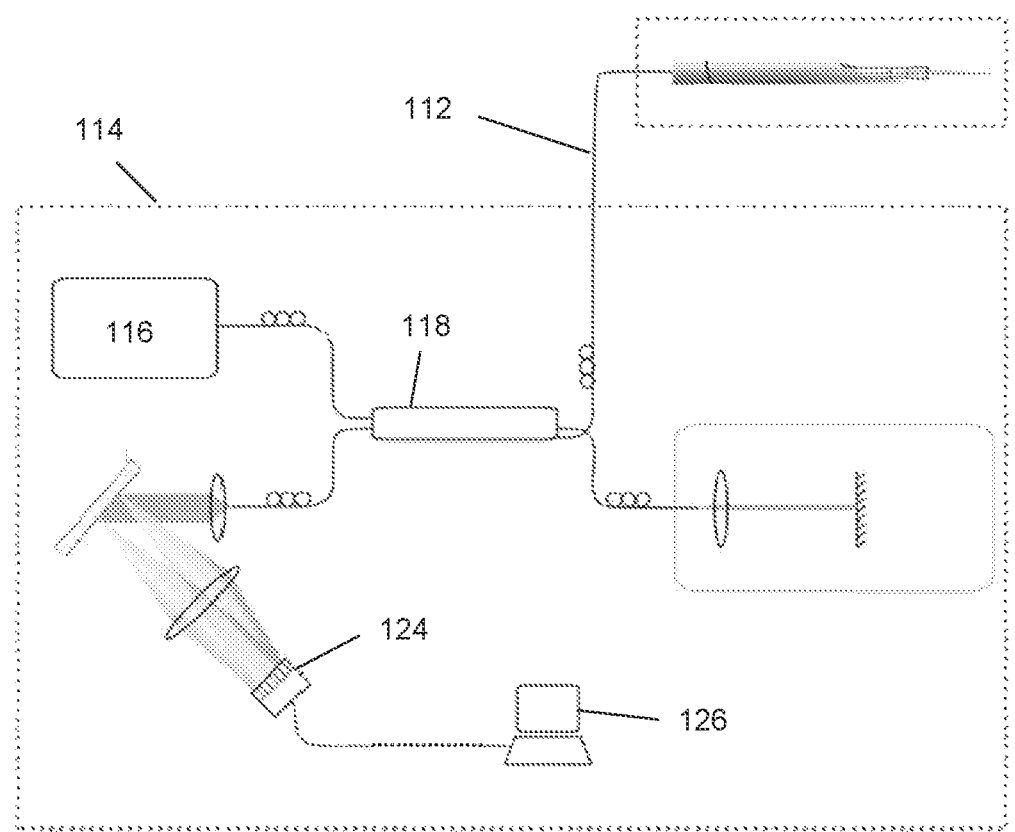
FIG. 3 is a schematic view of an optical processing system in accordance with an embodiment of the present invention.

The optical element 104 is connected to an optical fibre 112 as shown in FIGS. 1 and 3. The optical fibre 112 establishes communication with an optical processing system 114. In this particular example, the optical fibre 112 is a length of single mode fibre and the optical element 104 comprises a length of no-core optical fibre and a length of graded-index (GRIN) optical fibre spliced to a length of single-mode optical fibre (SMF). The combination of no-core and GRIN fibres acts as a lens shaping the near-infrared light 108 that is emitted from the optical element 104.

In the embodiment illustrated in FIG. 3, the optical processing system 114 is constructed in a manner that is similar to a Michelson interferometer. The optical processing system 114 comprises a broad band light source 116 for generating light and an optical beam splitter 118.

In this particular embodiment, the optical beam splitter 118 splits the light into two arms. Reference light is directed to a reference system and light is also directed into the deformable portion of the tissue 102. The optical beam splitter 118 may be a semi-transmissive mirror. Light of both arms propagate substantially the same length. A combination of the detected light at the optical element 104 and the reference light generate an interference pattern. A person skilled in the art will appreciate that different configurations are envisaged, such as a common-path configuration or single-arm configuration. The optical processing system 114 further comprises a CMOS detector 124 that converts the light of the interference pattern into digital data that can be further processed by a computer 126.

Referring now back to FIG. 1, the system 100 is arranged to characterise a mechanical property within the tissue 102 when the tip of the needle 106 with the optical element 104 is inserted into the deformable portion of the tissue 102. In this example, the method for characterising the mechanical property is conducted during deformation of the deformable portion of the tissue 102. However, a person skilled in the art will appreciate that the method may be conducted when the material is maintained in a deformed state or when the step of applying a force to deform the material is completed. In some embodiments, an additional measurement may be conducted before deformation of the material such that a difference of the detected electromagnetic radiation is indicative of the mechanical property.

When the tip of the needle 106 is advanced into, retracted from or rotated within the deformable portion of the tissue 102, the tip of the needle 106 applies a force to the tissue 102 and consequently deforms the portion of the tissue 102. The force may, for example, be friction between the tip of the needle 106 and the deformable portion of the tissue 102. A surface portion of the tip of the needle 106 may be modified to influence the friction between the tip of the needle 106 and the deformable portion of the tissue 102. For example, a coating may be applied to the surface portion of the needle so as to increase or decrease the friction between the tip of the needle 106 and the deformable portion of the tissue 102. The surface of the needle may be coated with a plurality of coatings such that the friction between the tip of the needle 106 and the deformable portion of the tissue 102 is a function of location on the surface of the tip of the needle 106.

A person skilled in the art will appreciate that deformation of the deformable portion of the material may be achieved by any suitable force, for example, by rotating the needle and/or periodically moving/rotating the needle tip.

A frequency of the periodic movements may be adjusted such that a characteristic deformation response and/or a resonant frequency for which a response of the deformation is relatively large can be acquired.

During deformation of the tissue 102 a mechanical property of the tissue 102 at the approximate location of the optical element 104 within the tip of the needle 106 can be characterised. In this particular example, the approximate location is a one-dimensional ray extending from the tip of the tip of the needle 106 to approximately 2 mm beyond the tip.

In another embodiment, the needle is rotated to deform tissue 102 surrounding the tip of the needle 106. The optical element 104 may, for example, emit the light 108 into the tissue 102 in a direction perpendicular to a central axis of the needle tip 106. This configuration enables characterising mechanical properties over a two-dimensional surface and therefore acquiring two-dimensional data.

A person skilled in the art will appreciate that the tissue 102 may be deformed by any suitable force. For example, the tissue 102 may be deformed by an internal force of a patient, such as cardiac motion or respiratory motion. Additionally or alternatively, a force may be applied to the tissue 102 by focused ultrasound beams, an external actuator, laser-induced shock waves or needle vibration.

The method in accordance with the embodiment shown in FIGS. 1 to 3 is conducted using optical coherence tomography. In an alternative embodiment, the method may be conducted using confocal fluorescence microscopy. Other imaging techniques may also be used, such as multi-photon microscopy, diffuse optical tomography, total internal reflection fluorescence microscopy, phase contrast microscopy, stimulated emission depletion microscopy, near-field scanning optical microscopy, differential interference contrast microscopy, and second harmonic imaging microscopy.

Detection of electromagnetic radiation may also be repeated at a particular location within the deformable material, for example, to indicate a response of the tissue to a particular medical treatment such as radiation therapy or chemotherapy.

In a further example, detection of electromagnetic radiation may be conducted at different locations when the tip of the needle 106 is inserted into the deformable portion of the tissue.

Figure 4:
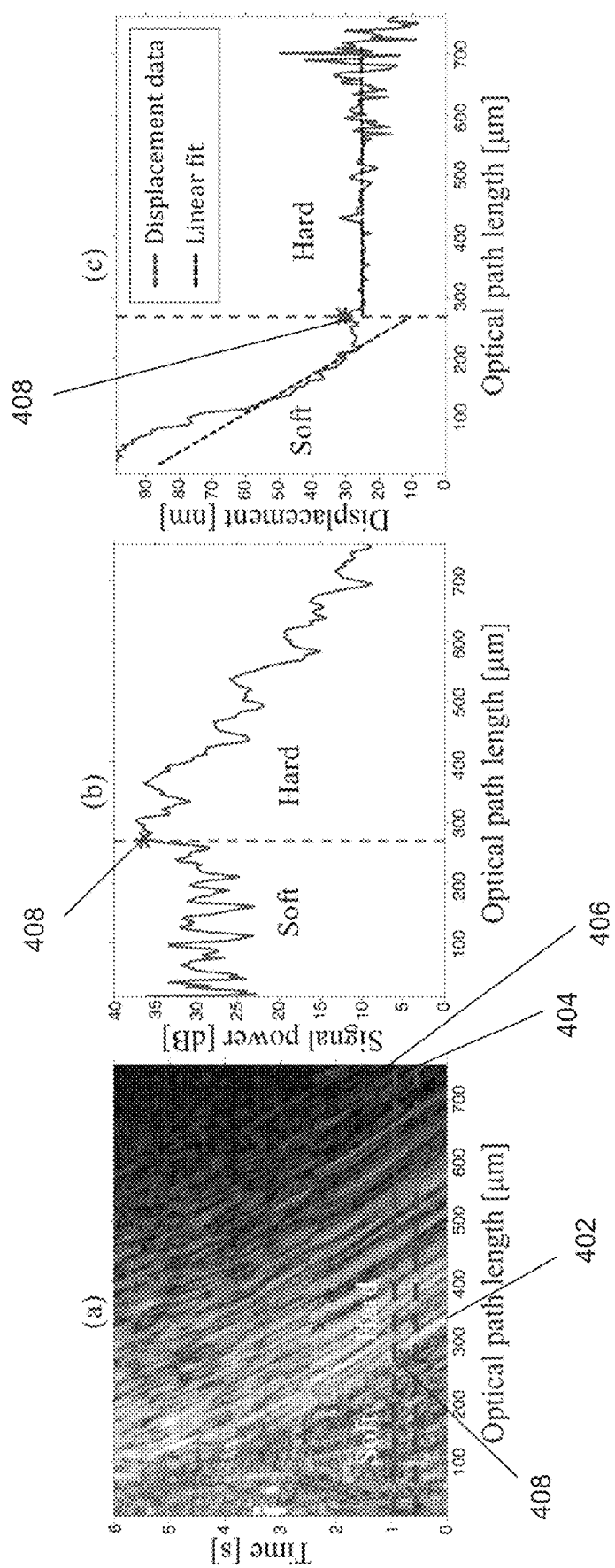
FIG. 4 shows data taken using a method in accordance with an embodiment of the present invention.
Figure 5:
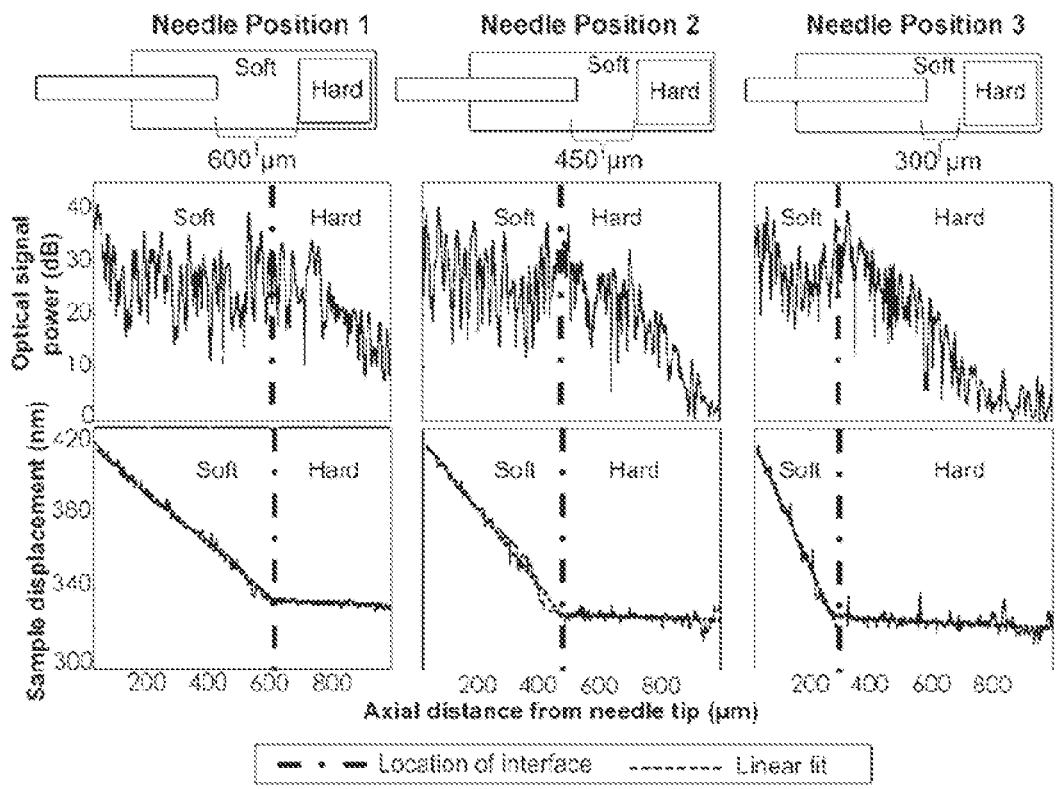
FIGS. 5 to 11 show data taken using a method in accordance with embodiments of the present invention.
Figure 6:
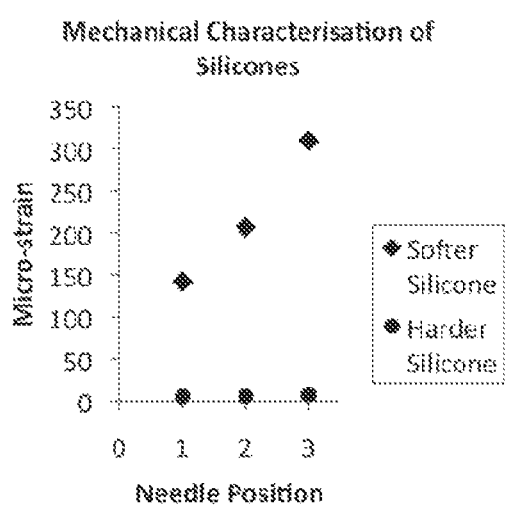

FIGS. 4 to 6 show an illustration of data that was acquired using the system 100 as shown and described with reference to FIGS. 1 to 3. The material 102 is silicone forming a medical "phantom". The phantom contains soft silicone having a known and distinct stiffness in which a portion of hard silicone with known and distinct stiffness was embedded ("inclusion").

In this particular embodiment, the system 100 is used for characterising an elasticity of the two portions of silicone material. As described above, the optical element 104 is arranged to emit and detect electromagnetic radiation in a direction that is parallel to the central axis of the tip of the needle 106. In other words, the imaging field of view is orientated parallel to the direction of the movement of the needle when the tip of the needle 106 is advanced into the silicone material 102. In this way, the optical element 104 measures movement in the silicone material 102 immediately beyond the needle tip 106 as it is inserted into the soft silicone material 102.

Electromagnetic radiation is detected at the optical element 104 when the tip of the needle 106 is advanced until the tip of the needle 106 reaches the interface of the two silicone materials. As the tip of the needle 106 is inserted, the tip of the needle simultaneously exerts a force on the silicone material in a manner such that a portion of the silicone material beyond the tip of the needle 106 is deformed.

As such, by analysing the detected electromagnetic radiation which in this embodiment is near infrared light, displacement of the silicone material 102 relative to the position of the tip of the needle 106 can be characterised. Local displacements of the silicone material are indicative of both Young's modulus and toughness of the material. Specifically, materials with high stiffness will undergo little deformation, while material with low stiffness will deform more easily.

By analysing the detected near-infrared light, the displacement of the silicone material of up to 1 mm in front of the tip of the needle 106 can be identified as the tip of the needle 106 is inserted. By further analysing the measured data, a location of the interface between the two silicone materials can be identified.

FIG. 4a) shows a motion-mode image that is associated with a sequence of measurements acquired when the tip of the needle 106 was inserted into the deformable portion of the tissue 102 over a period of time of 6 seconds. A motion-mode image may also be referred to as an M-mode image. Each horizontal row relates to light detected at different positions. In this particular embodiment, the emitted light is near-infrared light. Bright pixels indicate a relatively high degree of measured backscattered light. Dark pixels indicate a relatively low degree of measured backscattered light. FIG. 4a) illustrates a change in the texture of the backscattered light that is associated with the interface of the two silicone layers of the phantom (marked by a star 408).

The first measurement at a point in time indicated as 0 seconds indicates that the interface of the two silicone layers is approximately 330 µm in front of the tip of the needle 106. After 6 seconds the needle 106 has almost reached the interface of the two silicone layers. This interface may, for example, be associated with a boundary of a tumour.

FIG. 4b) shows a single backscatter profile that corresponds to an average of a plurality of backscatter profiles located between dashed lines 404 and 406 in FIG. 4a). The interface of the two silicone layers is marked by a star 408.

It can be seen in FIGS. 4a) and b) that the backscattering of the emitted light decreases with increasing optical path length.

FIG. 4c) shows a displacement profile. A displacement profile may, for example, be generated by speckle tracking or by measuring phase differences. An amount of displacement of the deformable portion of the tissue 102 decreases with increasing optical path length because the force applied by the tip of the needle 106 attenuates with increasing distance from the tip of the needle 106.

Local displacements of the tissue are indicative of both the Young's modulus and the toughness of the material. The rate at which the displacement decreases is determined by these properties. The displacement monotonically decreases in the soft silicone immediately adjacent to the tip of the needle 106. In contrast, the displacement remains substantially uniform in the rigid, hard layer of silicone. The interface between the two layers of silicone is marked with a star 408.

FIG. 5 shows data for three different positions 1 to 3 of the tip of the needle 106 within the deformable portion of the silicone material 102 while the tip of the needle 106 is advanced towards the hard portion of the silicone material. Schematic representations of the positions of the tip of the needle 106 relative to the hard silicone material are shown in the top row of FIG. 5. Single backscatter profiles similar to FIG. 4b) are illustrated for the respective three positions in the centre row of FIG. 5. The shown plots illustrate the optical signal versus the distance from the needle tip 106 at each position 1 to 3.

The plots in the bottom row of FIG. 5 illustrate the measured displacement versus the distance from the needle tip 106 at each position 1 to 3. The slope of the displacement data is indicative of the strain, and its magnitude depends on the stiffness of the sample (e.g. materials with a low stiffness undergo large deformation, which is quantified as high strain and appears as a large slope). Abrupt changes in strain are used to identify the interface between the soft and hard silicone material in each position. As such, at each needle position, the location of the interface between the two different silicone materials can be identified. The interface between the soft and hard silicone material is denoted by a dash-dot-dash line in each plot in FIG. 5.

As mentioned above, high strain (large deformation, indicated by a large slope on the displacement graph) corresponds to low stiffness, while low strain (small deformation, low slope) corresponds to high stiffness. The plot shown in FIG. 6 illustrates the strain in the soft and hard silicone material 102 measured at each position 1 to 3 of FIG. 5. Because the strain also depends on the thickness of the sample, the strain in the soft silicone increases as the tip of the needle 106 moves closer to the hard silicone, essentially reducing the thickness of the soft silicone ahead of the needle tip 106.

Figure 7:
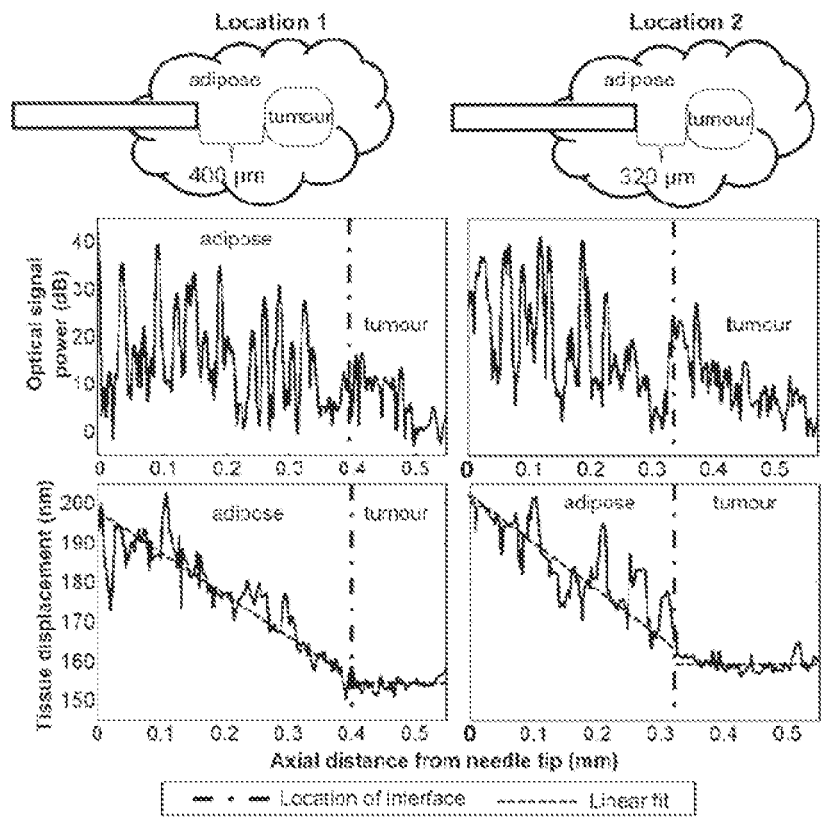
Figure 8:
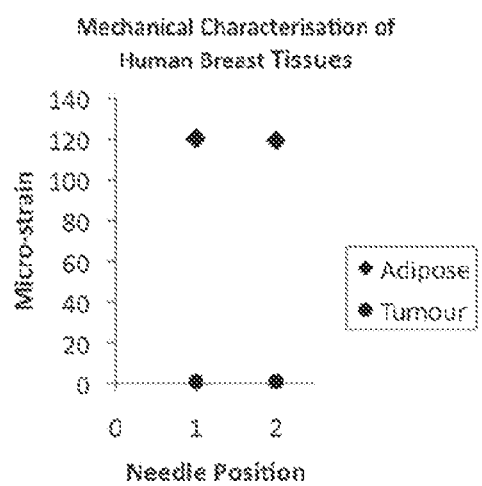

FIGS. 7 and 8 illustrate data acquired using the system 100 in a different material. In this particular embodiment, the material is human breast tissue comprising adipose (fat) and tumour tissue. The sample of breast tissue contains both healthy tissue and a stiff, cancerous tumour.

The tip of the needle 106 is inserted into healthy adipose (fat) breast tissue and advanced towards the tumour.

The detected optical signal and the sample displacement were measured ahead of the tip of the needle 106 at two locations within the breast tissue relative to the interface between the healthy tissue and the tumour. FIG. 7 shows schematics of each needle tip location within the breast tissue (top row), plots of the optical signal versus distance from the needle tip 106 at each location (middle row) and plots of the displacement versus distance from the needle tip 106 at each location (bottom row).

In the plot showing the optical signal (middle row), the change in tissue type corresponds to a change in the measured optical signal. There is great variation in the measured optical signal within the adipose (fat) healthy breast tissue, with each "high" signal corresponding to the outer walls of an adipose cell and the intervening lower signal corresponding to the body of the adipose cell. The optical signal varies much less in the tumour region.

In the displacement measurements (bottom row), abrupt changes in strain (indicated by the slope of displacement graph) are used to identify the interface between the adipose healthy breast tissue and the tumour in each needle tip position. As the tip of the needle 106 advances by 80 μm from location 1 to location 2, the identified interface between the healthy adipose tissue and the tumour which is denoted by a dash-dot-dash line in FIG. 7 draws closer to the needle by approximately 80 μm.

FIG. 8 illustrates the strain (slope) in the healthy adipose breast tissue and the tumour measured at each location of FIG. 7. The adipose breast tissue is characterized by high strain (low stiffness, large deformation), and the tumour by low strain (high stiffness, little deformation).

Figure 9:
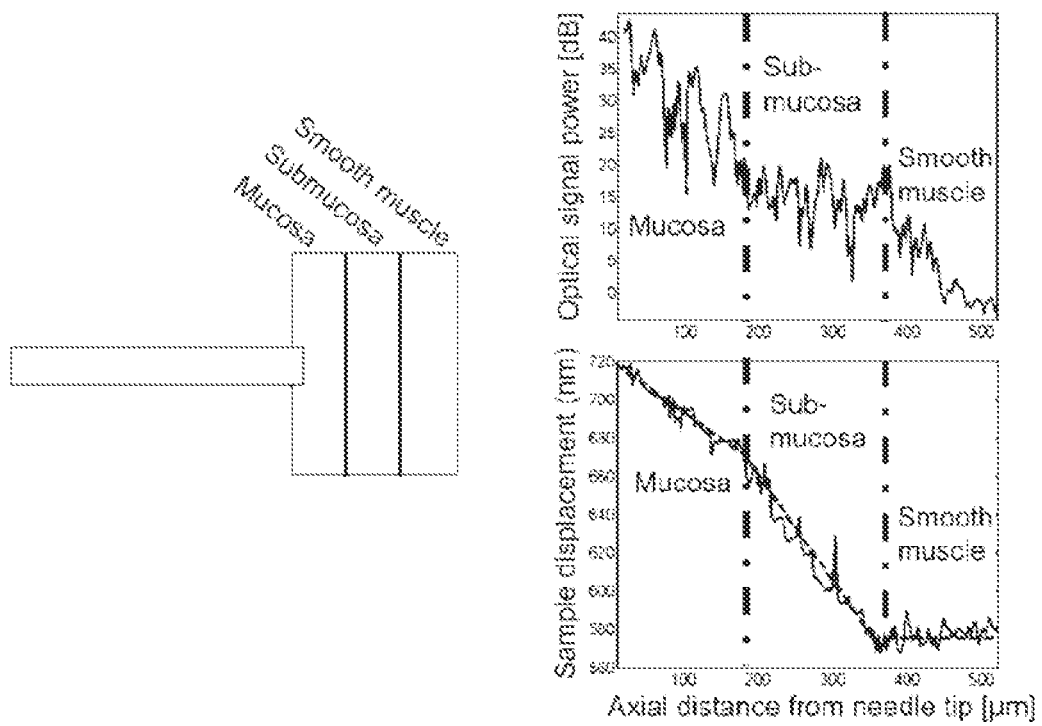
Figure 10:
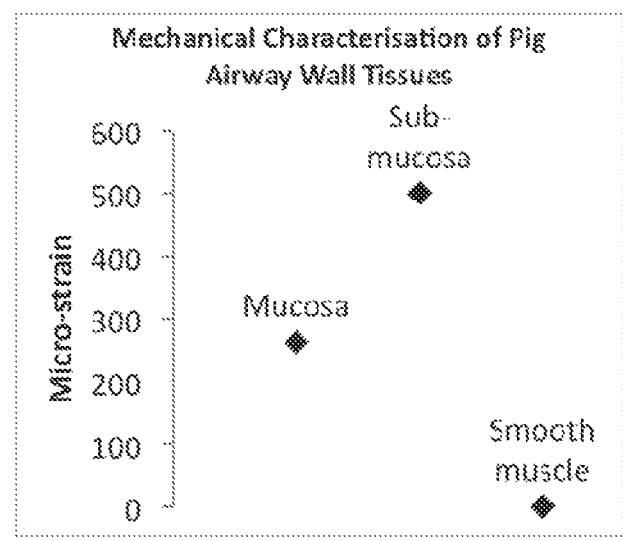

FIGS. 9 and 10 illustrate data acquired using the system 100 in an alternative material. In this particular example, the material is a sample of porcine (pig) tracheal wall tissue comprising three tissue layers, namely mucosa, submucosa and smooth muscle.

The tip of the needle 106 is inserted into the mucosa and indents the mucosa, submucosa and the smooth muscle tissue layers. In this example, measurements are acquired at a single position of the tip of the needle 106 relative to the interfaces between the different tissue layers. The method is conducted such that a location of the three tissue layers can be identified.

Similarly to the previous embodiments, the optical signal and the sample displacement were measured versus the distance beyond the tip of the needle 106. FIG. 9 shows a schematic representation of the position of the tip of the needle 106 within the tracheal wall tissue 102.

FIG. 9 further shows a plot of the optical signal (top right) and a plot of the sample displacement (bottom right) versus the distance from the needle tip 106 at the position of the tip of the needle 106 within the tissue 102. The interfaces between the three layers of tissue can be identified by changes in strain (i.e. changes in slope in the displacement plot). FIG. 9 shows that changes in the optical signal (top right) correspond well to changes in the slope of the displacement graph (bottom right).

The interfaces between mucosa, submucosa, and smooth muscle are denoted by a dash-dot-dash line in each plot.

FIG. 10 illustrates the strain (slope) in the mucosa, submucosa, and muscle tissue measured using this embodiment of the invention at the position shown in the schematic representation in FIG. 9. The mucosa and submucosa tissue layers are both characterized by high strain (low stiffness), and the muscle tissue layer by low strain (high stiffness).

Figure 11:
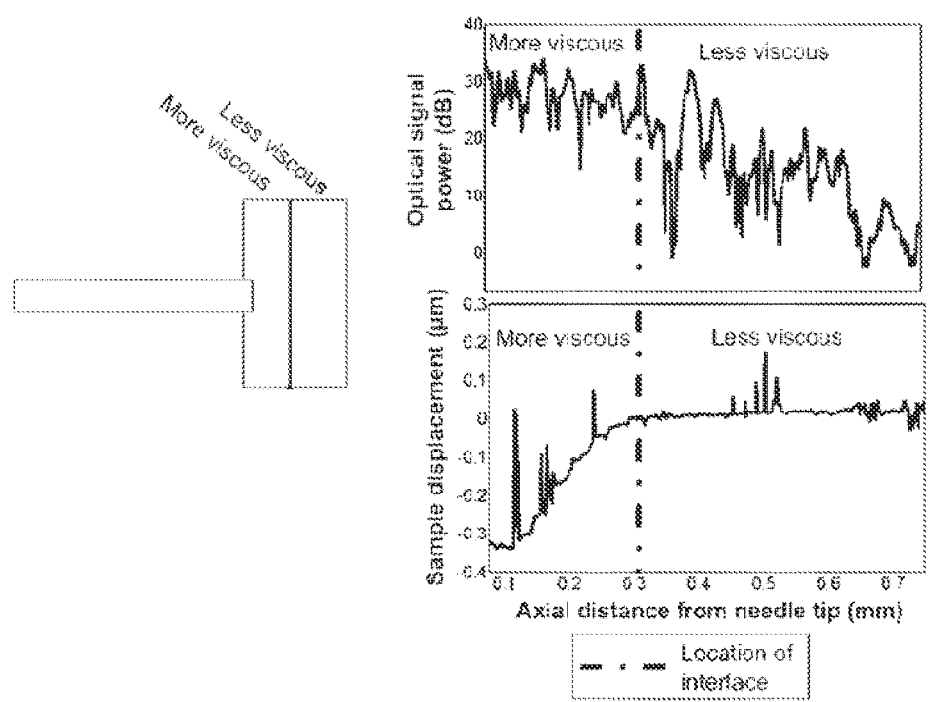

FIG. 11 illustrates data acquired using the system 100 for performing the method in accordance of an alternative embodiment of the invention. In this particular embodiment, the method is conducted to characterise a viscoelasticity of a material. The material in this example is silicone forming a medical "phantom". The phantom contains two layers of silicone material. The first layer of silicone material has a higher viscosity than the second layer.

A person skilled in the art will be aware that viscosity refers to a mechanical property of a material which describes how the material will continue to deform following application of a load. For example, a highly viscous material will continue to deform with time (also denoted as material creep or relaxation) and a material having a low viscosity will change relatively little following an applied force to deform the material.

The tip of the needle 106 is inserted into the layer of highly viscous silicone, then advanced over a short distance towards the less viscous layer of silicone material, and then held at a fixed location.

In this particular embodiment, the optical element 104 measures displacement of the material beyond the tip of the needle 106 for one second after movement of the tip of the needle 106 within the silicone material is terminated.

The measured displacement is attributed to a mixture of the elastic response of the silicone material (instantaneous displacement with an applied force), and viscous response of the material (time-dependent displacement after movement of the needle is terminated). Thus, the total measured displacement is indicative of the viscoelastic properties of the material.

FIG. 11 shows a schematic representation of the needle tip position within the silicone material wherein the first layer of silicone is denoted as "more viscous" and the second layer of silicone which has a lower viscosity than the first layer is denoted as "less viscous". FIG. 11 further illustrates a plot showing the detected optical signal versus the distance from the needle tip (top right) and a plot showing the displacement versus the axial distance from the needle tip (bottom right) measured at the position shown in the schematic representation.

The optical signal and displacement are measured for one second after movement of the tip of the needle 106 was terminated. Within this time, the first silicone layer having the higher viscosity continued to change its displacement (seen as a negative, or backward displacement toward the needle tip), and the silicone layer having a lower viscosity remained stationary. This change in the trend of the displacement can be used to identify the interface between the more viscous and less viscous silicone layers.

The rate of relaxation of the material provides quantification of the viscosity of the material. A material with no viscosity (a purely elastic material) will instantaneously converge to its final stable position when exposed to a mechanical force to deform the material. A material with low viscosity will continue to undergo displacement for a relatively short period of time following application of the deforming force. A highly viscous material will continue to displace for a relatively large amount of time following application of the force.

By using the displacement graph in FIG. 11 (bottom right) to quantify the amount of displacement over a fixed period of time following application of the deforming force, it can be quantified that the silicone layer that is closer to the tip of the needle 106 has a relatively high viscosity compared to the adjacent layer of silicone material which has a relatively low viscosity.

By combining measurements of the elasticity of the material (by quantifying the rate of change of displacement with distance from the needle, as shown in the previous embodiments) with measurements of viscosity (amount of displacement over a fixed period of time once the movement of the tip of the needle has stopped), the viscoelastic properties of the materials can be characterised.

The interface between the two layers of silicone material is denoted by a dash-dot-dash line in each plot.

Figure 12:
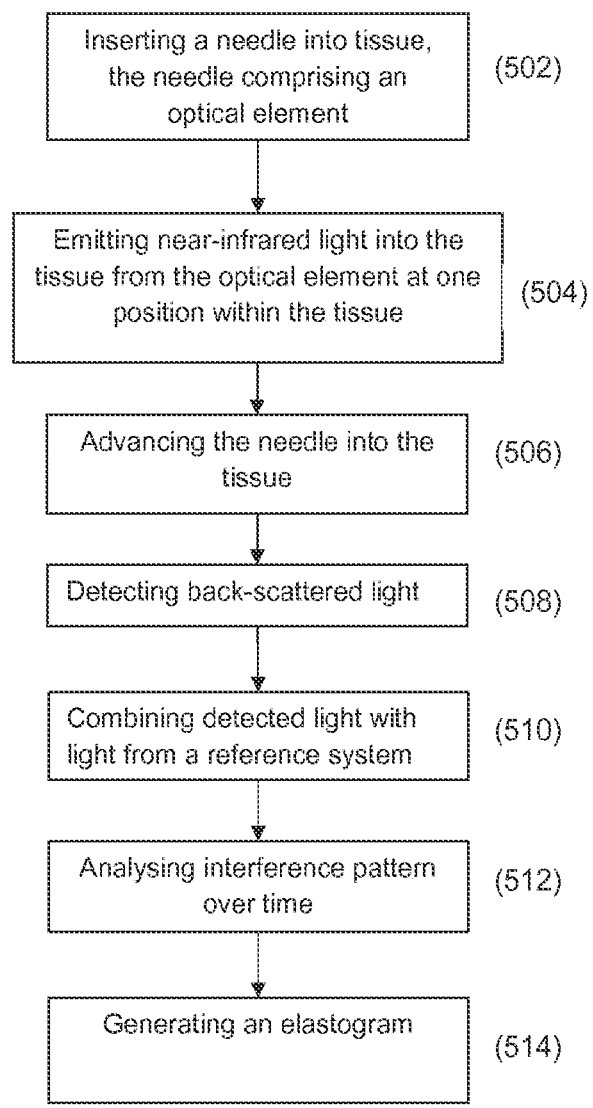
FIG. 12 is a flow chart of a method in accordance with an embodiment of the present invention.

FIG. 12 shows a flow diagram of a method 500 in accordance with an embodiment of the present invention. In a first step 502, the tip of the needle 106 comprising the optical element 104 is inserted into the deformable portion of the tissue 102. By inserting the tip of the needle 106 into the deformable portion of the tissue 102, the tip of the needle 106 applies a mechanical force to the deformable portion of the tissue 102 such that the portion of the tissue 102 is deformed.

In a second step 504 near-infrared light 108 is emitted into the deformed portion of the tissue 102 from the optical element 104 in a direction that is parallel to a central axis of the tip of the needle 106. A portion of the emitted light 108 interacts with the portion of the tissue 102 within a particular distance from the tip of the needle 106 and is being backscattered to the optical element 104. In a third step 506, the tip of the needle 106 is advanced into the deformable portion of the tissue over time. The optical element 104 detects the backscattered light in step 508. The detected signal corresponds to a plurality of locations within the tissue because the backscattered light is detected while the tip of the needle 106 is advanced into the tissue. In step 510 the detected light is transmitted to an optical processing system where the detected light is combined with light from a reference system. In step 512 the combined light is converted into digital data and an elastogram is generated, wherein displacement at locations in the material is illustrated by brightness of pixels.

The elastogram may be further analysed to characterise the tissue in front of the tip of the needle and/or to identify a boundary between healthy and diseased tissue.

Although the invention has been described with reference to particular examples, it will be appreciated by those skilled in the art that the invention may be embodied in many other forms.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

What is claimed is:

1. A method comprising:
   providing a biological tissue having a deformable portion;
   providing a device having an insertion portion that is arranged for insertion into the deformable portion,
      the insertion portion having a tip and comprising at the tip a surface that has a coating that is arranged to decrease friction between the insertion portion and the deformable portion compared with friction between the insertion portion and the deformable portion without the coating,
      the device further comprising an optical fibre portion that is configured to transmit electromagnetic radiation from the device into the deformable portion and to receive electromagnetic radiation backscattered from a location within the deformable portion, the optical fibre portion being connected to an optical processing system configured to emit the electromagnetic radiation and detect the backscattered electromagnetic radiation;
   deforming the deformable portion by moving the insertion portion of the device within the deformable portion;
   emitting the electromagnetic radiation using the optical processing system;
   transmitting the electromagnetic radiation to the location within the deformable portion using the optical fibre portion while the deformable portion is being deformed by movement of the insertion portion;
   receiving the backscattered electromagnetic radiation from the location within the deformable portion;
   detecting the backscattered electromagnetic radiation from the location within the deformable portion in response to the emitted electromagnetic radiation using the optical processing system;
   processing the detected electromagnetic radiation to derive information indicative of a deformation of the deformable portion resulting from moving the insertion portion of the device within the deformable portion of the biological tissue; and
   identifying, based on the information derived from the detected electromagnetic radiation, a relative displacement of the biological tissue at each of a plurality of distances from a position of the tip of the insertion portion, the relative displacement of the biological tissue being associated with the mechanical property of the biological tissue; and
   identifying a location of an interface between different biological tissue types based on differences in the relative displacement of the biological tissue at the different distances from the position of the tip of the insertion portion.

2. The method of claim 1, further comprising:
   detecting the backscattered electromagnetic radiation in response to the emitted electromagnetic radiation during and after the deformation at the location within the deformable portion of the material using the optical processing system; and
   comparing a quantity indicative of the backscattered electromagnetic radiation detected during the deformation with a quantity indicative of the backscattered electromagnetic radiation detected after the deformation to produce a result that is indicative of the mechanical property of the material.

3. The method of claim 1 wherein the mechanical property is one of: an elasticity, a viscosity and a viscoelasticity.

4. The method of claim 1 wherein the insertion portion of the device comprises an elongate body and a flat end in a plane perpendicular to a longitudinal axis of the elongate body.

5. The method of claim 4 wherein moving the insertion portion within the deformable portion of the biological tissue comprises advancing and/or retracting and/or rotating the insertion portion in one or more direction(s) within the deformable portion of the biological tissue.

6. The method of claim 1 wherein the method further comprises characterising the biological tissue as healthy or diseased tissue based at least in part on the relative displacement of the biological tissue.

7. The method of claim 6 comprising characterising the diseased tissue based at least in part on the relative displacement of the biological tissue.

8. The method of claim 6 comprising identifying a location of the diseased tissue based at least in part on the relative displacement of the biological tissue.

9. The method of claim 1 wherein the method further comprises providing an acoustic or a visual indication of a presence of diseased tissue based at least in part on the relative displacement of the biological tissue.

10. The method of claim 1 wherein the method is conducted during surgery of a patient to characterise a diseased tissue based at least in part on the relative displacement of the biological tissue.

11. The method of claim 1, further comprising:
    positioning the device relative to the biological tissue;
    determining whether the biological tissue at the location includes cancerous tissue based at least in part on the displacement of the biological tissue relative to the position of the tip of the insertion portion; and
    defining the delineation of the cancerous tissue based on a plurality of determined displacements of the biological tissue at a plurality of different locations.

12. The method of claim 1, wherein identifying the location of the interface between the different biological tissue types includes identifying an abrupt change in a slope of a graph of tissue displacement as a function of distance from the tip of the insertion portion.

13. The method of claim 1, wherein providing the device having the insertion portion further includes providing a needle with an exterior surface, wherein different location on the exterior surface along a length of the needle are coated with different friction-influencing coatings such that friction between the exterior surface of the needle and the deformable portion of the tissue is a function of location along the length of the needle.

14. A device for analyzing biological tissue, a portion of the biological tissue being deformable, the device comprising:
- an insertion portion for insertion into the deformable portion of the biological tissue, the insertion portion having a surface arranged to deform the deformable portion;
- an optical fibre arranged to transmit electromagnetic radiation from the device into the deformable portion of the biological tissue and to receive electromagnetic radiation backscattered from a location within the deformable portion while the deformable portion is being deformed by movement of the insertion portion, the optical fibre being positioned at least partially within the insertion portion, and the optical fibre being connected to an optical processing system configured to emit the electromagnetic radiation and detect the backscattered electromagnetic radiation; and
- an electronic processor configured to identify a displacement of the biological tissue relative to a position of the tip of the insertion portion using information derived from the detected backscattered electromagnetic radiation, the displacement of the biological tissue being associated with the mechanical property of the biological tissue,
- wherein the insertion portion has a tip and comprises at the tip a surface that has a coating arranged to decrease friction between the insertion portion and the deformable portion compared with friction between the insertion portion and the deformable portion without the coating,
- wherein the electronic processor is configured to identify the displacement of the biological tissue relative to the position of the tip of the insertion portion by identifying, based on the detected electromagnetic radiation, the relative displacement of the biological tissue at each of a plurality of different distances from the position of the tip of the insertion portion, and
- wherein the electronic processor is further configured to identify a location of an interface between different biological tissue types based on differences in the relative displacement of the biological tissue at the different distances from the position of the tip of the insertion portion.

15. The device of claim 14, wherein the insertion portion of the device comprises an elongate body and a flat end in a plane perpendicular to a longitudinal axis of the elongate body.

16. The device of claim 14, wherein the insertion portion includes an elongate body with an exterior surface, wherein the exterior surface of the elongate body includes a friction-influencing coating with a plurality of different coating portions at different locations along a length of the elongate body, wherein each different coating portion of the plurality of different coating portions provides a different friction-influencing property such that friction between the exterior surface of the elongate body and the deformable portion of the tissue is a function of location along the length of the elongate body.

17. The device of claim 14, wherein the electronic processor is configured to identify the location of the interface between the different biological tissue types by identifying an abrupt change in a slope of a graph of tissue displacement as a function of distance from the tip of the insertion portion.

* * * * *